United States Patent
Osborn, III et al.

(10) Patent No.: US 6,261,277 B1
(45) Date of Patent: *Jul. 17, 2001

(54) ABSORBENT INTERLABIAL DEVICE

(75) Inventors: Thomas Ward Osborn, III, Cincinnati; Pamela Jean Brown, Maineville; Ronald Ray McFall, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,269

(22) Filed: Jun. 11, 1999

Related U.S. Application Data

(63) Continuation of application No. 08/970,510, filed on Nov. 14, 1997, now Pat. No. 5,968,026, which is a continuation-in-part of application No. 08/883,606, filed on Jun. 26, 1997, now Pat. No. 5,762,644, and a continuation-in-part of application No. 08/876,206, filed on Jun. 16, 1997, and a continuation-in-part of application No. 08/869,897, filed on Jun. 5, 1997, and a continuation-in-part of application No. 08/778,520, filed on Jan. 3, 1997, now Pat. No. 5,895,381, and a continuation-in-part of application No. 08/778,925, filed on Jan. 3, 1997, now abandoned, and a continuation-in-part of application No. 08/778,521, filed on Jan. 3, 1997, and a continuation-in-part of application No. 08/706,371, filed on Aug. 30, 1996, now Pat. No. 5,885,265.

(51) Int. Cl.[7] ....................................... A61F 13/15
(52) U.S. Cl. ........................................... 604/385.17
(58) Field of Search ................... 604/904, 378, 604/330, 363, 385.17, 385.18

(56) References Cited

U.S. PATENT DOCUMENTS

| | | | |
|---|---|---|---|
| 3,706,311 | * 12/1972 | Kokx et al. | 604/904 |
| 5,403,300 | * 4/1995 | Howarth | 604/904 |
| 5,702,380 | * 12/1997 | Walker | 604/385.17 |
| 5,968,026 | * 10/1999 | Osborn, III et al. | 604/378 |
| 5,968,027 | 10/1999 | Cole et al. | |

* cited by examiner

*Primary Examiner*—Dennis Ruhl
(74) *Attorney, Agent, or Firm*—Matthew P. Fitzpatrick

(57) ABSTRACT

An absorbent interlabial device that is worn interlabially by female wearers for catemenial purposes, incontinence protection, or both, is disclosed. The absorbent interlabial device of the present invention is characterized by improved wearing comfort and increased capacity as compared to known interlabial devices. The absorbent interlabial device of the present invention includes at least an central absorbent portion (or core) surrounded by a liquid pervious topsheet. The topsheet is folded laterally inward over the central absorbent portion and downward to form a central groove on the top surface of the interlabial device. The central groove faces toward the vestibule of the wearer upon insertion into the interlabial space. The central groove improves the comfort associated with the wearing of the interlabial device, and allows the device to more rapidly acquire fluids, particularly viscous fluids. Additional features of the device may include a pair of flexible extensions, a secondary topsheet for improve acquisition rate, and tapered sealed ends for improved wearing comfort.

3 Claims, 5 Drawing Sheets

ABSORBENT INTERLABIAL DEVICE

CROSS REFERENCE TO RELATED APPLICATIONS

This is a continuation of Ser. No. 08/970,510 filed on Nov. 14, 1997, now U.S. Pat. No. 5,968,026, which is continuation in part of the following: Ser. No. 08/883,606 filed on Jun. 26, 1997, now U.S. Pat. No. 5,762,644; Ser. No. 08/876,206 filed on Jun. 16, 1997, pending; Ser. No. 08/869,897 filed on Jun. 5, 1997, pending; Ser. No. 08/778,520 filed on Jan. 3, 1997, now U.S. Pat. No. 5,895,381; Ser. No. 08/778,925 filed on Jan. 3, 1997, abandoned; Ser. No. 08/778,521 filed on Jan. 3, 1997, pending; and Ser. No. 08/706,371 filed on Aug. 30, 1996, U.S. Pat. No. 5,885,265.

FIELD OF THE INVENTION

This invention relates to absorbent devices, and more particularly to an improved absorbent device that is worn interlabially by female wearers for catamenial purposes, incontinence protection, or both.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. No. 5,484,429 issued to Vukos, et al. on Jan. 16, 1996. A commercially available interlabial device is the FRESH 'N FIT PADETTE® which is marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

Many of these interlabial devices have not met with great commercial success, however. There are drawbacks associated with performance, comfort, or both with respect to the above products. For example, the device described in the Delaney patent does not appear to be capable of an easy and comfortable insertion, due to the possibility of the layers of absorbent material opening up during insertion. The commercially available PADETTES suffer from the disadvantage that they may not provide sufficient capacity for catamenial protection during heavier flow times. The device described in the Vukos et al. patent requires an external storage module to achieve the capacity described and may have comfort drawbacks in comparison to the absorbent interlabial device of the present invention.

Thus, a need exists for an interlabial device that is small in size and that can be easily inserted and that provides protection against incontinence, menstrual discharges, and discharges of bodily exudates throughout a great range of wearer motions and under a broad range of flow conditions. A need also exists for an interlabial device with an improved acquisition rate especially with respect to more viscous discharges. Ideally, an interlabial device should be highly comfortable, have a high capacity, be easy to insert and remove, and be toilet-disposable. A need also exists for an interlabial device which fulfills these needs and which also may be readily manufactured using current web handling technology.

Therefore, it is an object of the present invention to provide a high capacity, comfortable absorbent interlabial device which is small in size and is easy to insert.

It is another object of the present invention to provide an absorbent interlabial device capable of rapid acquisition of fluid, especially more viscous fluid.

It is another object of the present invention to provide an absorbent interlabial device that consistently blocks the urethra and the orifice of the vagina so that it provides protection against incontinence, menstrual discharges, and discharges of bodily exudates throughout a great range of wearer motions.

It is another object of the present invention to provide an absorbent interlabial device that can be inserted interlabially without the wearer's hand touching the inner surfaces of the labia.

It is another object of the present invention to provide an absorbent interlabial device that will reliably be expelled when the wearer urinates so that the wearer does not have to touch the soiled product.

It is another object of the present invention to provide an absorbent interlabial device that may optionally be removed with the fingers without the wearer's hand touching the inner surfaces of the labia.

It is another object of the present invention to provide an absorbent interlabial device which maintains sufficient integrity while it is worn such that it does not disintegrate or tear in use.

It is another object of the present invention to provide an absorbent interlabial device which may be easily disposed of in a conventional toilet.

It is another object of the present invention to provide an absorbent interlabial device which meets the above described objects and which may be conveniently manufactured using current web handling technology.

These and other objects of the present invention will become more readily apparent when considered in reference to the following description and when taken in conjunction with the accompanying drawings.

SUMMARY OF THE INVENTION

This invention relates to absorbent devices, and more particularly to an absorbent device that is insertable into the interlabial space of a female wearer for catamenial purposes, incontinence protection, or both.

The absorbent interlabial device of the present invention preferably comprises a central absorbent portion and a liquid pervious topsheet wrapped around the central absorbent portion. The length of the absorbent interlabial device is greater than the width of the absorbent interlabial device. The topsheet is folded laterally inward over the central absorbent portion and downward substantially in the z-direction. This folding defines a central groove substantially oriented in the z-direction which extends in the x-direction along at least a portion of the length of the absorbent interlabial device. The groove faces toward the vestibule floor of the wearer upon insertion of the absorbent interlabial device into the interlabial space of the wearer.

In preferred embodiments, the longitudinal cross section (i.e. the cross-section looking into the y-z plane) of the absorbent device is generally of a cardiod or heart-shape. The cross-sectional shape of the absorbent device may also be described as two U-shaped folds at the upper surface of the device which define a central groove. The bottom surface of the device is characterized by a single, larger, U-shaped fold.

In an additional preferred embodiment, of the present invention, the device also comprises a pair of flexible extensions joined to the liquid pervious topsheet and extending outward. Preferably, the flexible extensions are capable of maintaining contact with the inside surfaces of the wearer's labia when the absorbent device is worn. The flexible extensions are also preferably capable of covering the wearer's fingertips as the absorbent device is inserted into the interlabial space of the wearer.

In one preferred embodiment, the device may include a liquid impervious backsheet joined to at least a portion of the topsheet.

In yet other preferred embodiments, the absorbent device may comprise a slitted core for increased flexibility. Additionally, the absorbent device may comprise a secondary acquisition layer disposed between the central absorbent portion and the liquid pervious topsheet.

In one preferred embodiment, the longitudinal edges of the topsheet are sealed so as to form an absorbent device with sealed ends. In preferred embodiments of the present invention, these sealed ends are oriented in the z-direction. In more preferred embodiments, the sealed ends are also oriented in a longitudinally outward to inward relationship when viewed from a downward to upward relationship along the height of the device. The device in such preferred embodiments has a generally trapezoidal shaped transverse cross section.

In yet additional preferred embodiments the absorbent device is flushable. Preferably, the absorbent device is at least partially constructed from biodegradable materials. Additionally, the absorbent interlabial device will preferably disperse into at least two, and more preferably into several fragments within two hours of exposure to mildly agitated room temperature water.

In preferred embodiments, about one-half of the absorbent device resides within the interlabial space of the wearer upon insertion. The absorbent interlabial device, in preferred embodiments, blocks the wearer's urethra and orifice of the vagina upon insertion.

A preferred method of making the absorbent device of the present invention includes the steps of providing a piece of topsheet material, laying a piece of central absorbent material atop of the topsheet material, folding the edges of both the topsheet material and central absorbent material as a unit inwardly and downwardly to define a central groove, and securing the folded material to form an absorbent interlabial device having an upwardly oriented central groove.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
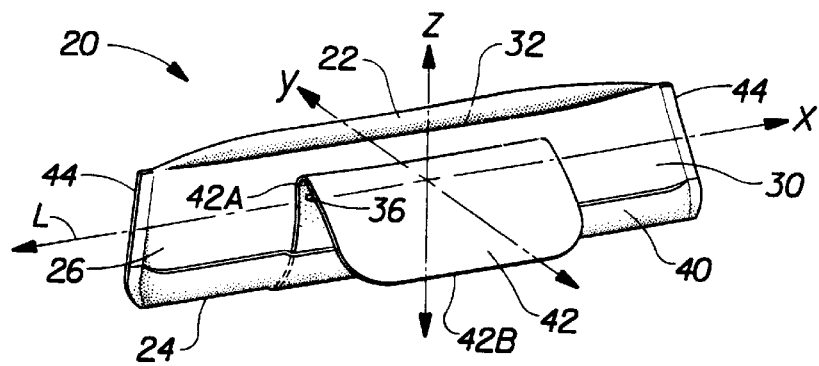
FIG. 1 is a perspective view of a preferred embodiment of the absorbent interlabial device of the present invention.

The present invention is directed to an absorbent interlabial device. FIG. 1 shows one preferred embodiment of the absorbent interlabial device of the present invention, absorbent interlabial device 20. The present invention, however, can be in many other forms, and is not limited to a structure having the particular configuration shown in the drawings.

As used herein the term "absorbent interlabial device" refers to a structure which has at least some absorbent components, and is specifically configured to reside at least partially within the interlabial space of a female wearer during use. Preferably, about one-half of the entire absorbent interlabial device 20 of the present invention resides within such interlabial space, more preferably more than one-half of the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and labia minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at 1025–1027.

Figure 2:
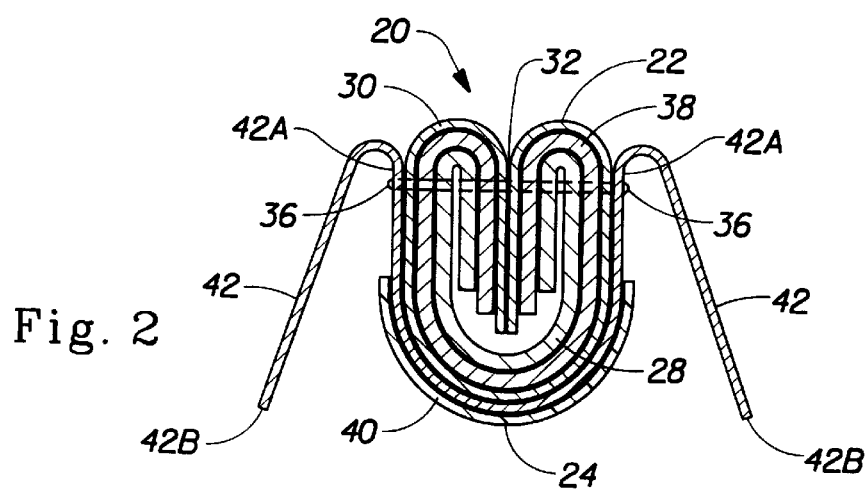
FIG. 2 is a cross-sectional end view of the absorbent device shown in FIG. 1.

A preferred embodiment of the absorbent interlabial device 20 of the present invention is shown in FIGS. 1 and 2. FIG. 2 is a cross-sectional view of the interlabial device 20 shown in FIG. 1. When viewed in conjunction with each other, FIGS. 1 and 2 most clearly show the components making up the interlabial device 20.

The absorbent interlabial device 20 has a longitudinal centerline L which runs along the "x" axis shown in FIG. 1. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The "length" of the interlabial device 20 is the linear measurement of the interlabial device 20 taken in the x-direction. The terms "transverse," "lateral," or "y direction" as used herein, are interchangeable, and refer to a line axis or direction that is generally perpendicular to the longitudinal direction. The lateral direction is shown in FIG. 1 as the "y" direction. The "width" of the interlabial device 20 is the linear measurement of the interlabial device 20 taken in the y-direction. The "z" direction, shown in FIG. 1, is a direction parallel to the vertical plane described above. The term "upper" refers to an orientation in the z-direction toward the wearer's head. "Lower" or downwardly is toward the wearer's feet. The "height" of the interlabial device 20 is the linear measurement of the interlabial device 20 taken in the z-direction.

The absorbent interlabial device 20 of the present invention includes at least a main portion 26 having a top surface 22 and a bottom surface 24. In use, the top surface 22 is furthest inserted into the interlabial space of the wearer. The main portion 26 preferably comprises at least a central absorbent portion 28 (also referred to as an "absorbent core" or "main absorbent portion") and a liquid pervious topsheet 30. The topsheet 30 is folded laterally inward over the central absorbent portion 28 and downward substantially in the z-direction. This folding defines a central groove 32 generally disposed along the top surface 22 of the interlabial device 20. The central groove 32 extends in the x-direction along at least a portion of the length of the interlabial device 20.

The central groove 32 is substantially oriented in the z-direction, that is the space between the edges of the topsheet 30 which defines the central groove 32 is generally oriented in an up and down direction starting from the top surface 22 of the interlabial device 20 and running downwardly into the main portion 26 of the interlabial device 20. The central groove 32 faces toward the vestibule floor of the wearer upon insertion of the absorbent interlabial device into the interlabial space of the wearer.

The central groove 32 of the present invention allows the interlabial device 20 acquire fluids more quickly than prior art devices. Fluids, as defined herein refers to liquids which may include viscous material and solids. Particularly when exposed to more viscous fluids, the central groove 32 will reduce the tendency of the interlabial device 20 to act as a "stop" or a "plug" and be more receptive to body exudates as compared to prior art devices. The central groove 32 also allows the top surface 22 of the interlabial device 20 to more easily fit around the clitoris. This ability of the central groove 32 to fit around the clitoris improves the level of comfort associated with the wearing of the device 20 within the wearer's interlabial space.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially intercepts, and more preferably completely intercepts and absorbs the flow of menses, urine, and other bodily exudates from the wearer's vaginal orifice and urethra.

The size of the interlabial device 20 is also important to the comfort associated with wearing the device. The length of the absorbent interlabial device 20 is greater than the width of the absorbent interlabial device 20. In the preferred embodiment shown in FIGS. 1 and 2, the main portion 26 of the interlabial device 20 has a length as measured along the longitudinal centerline, L, of between about 60 mm and about 120 mm. Preferably, the length of the interlabial device 20 is between about 80 mm and about 110 mm, and more preferably, is about 100 mm. The caliper (or width) of the main portion 26 of the interlabial device 20 as measured in the transverse direction (or "y"-direction) is preferably between about 4.5 and 15 mm, more preferably the caliper is about 8 mm. Caliper measurements given herein were measured using an AMES gage with a 0.25 psi (1.7 kPa) (gauge) load and a 0.96 inch diameter foot. Those skilled in the art will recognize that if a 0.96 inch diameter foot is not appropriate for a particular sample size, the foot size may be varied while the load on the gauge is accordingly varied to maintain a confining pressure of 0.25 psi (1.7 kPa)(gauge). The height (or "z"-direction dimension) of the main portion 22 is preferably between about 10 mm and about 30 mm, and more preferably is about 19 mm.

The interlabial device 20 is preferably provided with sufficient absorbency to absorb and retain the exudates discharged from the wearer's body. The capacity of the product, however, is dependent at least partially upon the physical volume of the absorbent interlabial device 20, particularly the main portion 26 thereof. The main portion 26 preferably has a capacity of at least about 3 g of 0.9% by weight saline solution, and may have a capacity of up to about 20 g by using absorbent gels or foams that expand when wet. Capacities may typically range from about 5 to about 10 grams, for saline. Those skilled in the art will recognize that the capacity for absorption of body exudates such as menses will typically be smaller than the capacities given above for absorption of saline, particularly if a superabsorbent material is used. A method for measuring absorbent capacity is described in the TEST METHODS section, below. Since the interlabial space can expand, larger volumes can be stored in the interlabial space, if the fluid is stored as a gel, which adjusts to the body pressures. Additionally, if the interlabial device 20 does not reside completely within the wearer's interlabial space, some of the absorbed exudates may be stored externally to the wearer's interlabial space.

As noted previously, the main portion 26 of the interlabial device 20 preferably comprises at least a liquid pervious topsheet 30 which is wrapped around a central absorbent (or core) portion 28. The central absorbent portion 28 of the preferred embodiment shown in FIGS. 1–2 may be manufactured from a wide variety of liquid-absorbent materials commonly used in absorbent articles. The central absorbent portion 28 is preferably constructed from a material which is flexible, and has a high absorbency. In preferred embodiments of the present invention, the central absorbent portion 28 will provide at least about 70% of the absorbent capacity of the interlabial device 20. The remainder of the capacity may reside in other features of the device 20, such a secondary topsheet 38 or flexible extensions 42. Sufficient absorbency may be obtained through the use of superabsorbent polymers in either particulate or fibrous form.

A suitable material for the central absorbent portion 28 is a thermally bonded airlaid material (TBAL) available from Technical Absorbents, Ltd. of Grismby, UK which incorporates about 40% OASIS superabsorbent fibers (available from Lantor, Ltd. of Bolton, England). This material has an overall basis weight of about 150 g/m². Another suitable material is a TBAL material which incorporaes about 17.5% FIBERDRI superabsorbent fibers. The material has a basis weight of about 120 g/m² and is available from Camelot Technologies, Ltd. of South High River, Alberta, Canada. (All percentages are by weight unless otherwise noted.)

A third suitable material for the central absorbent portion 28 is a TBAL material with available from Merfin Hygienic Products of Delta, British Columbia, Canada. This material has a basis weight of less than about 150 g/m² and incorporates about 15% absorbent gelling material (AGM) by weight. Somewhat higher amounts of AGM are also acceptable. The central absorbent portion 28, may also be contructed from Galaxy rayon which is available from Courtaulds Fibers/Allied Colloids (a joint venture company) of London, England. Additionally, a blend of Galaxy rayon and cotton may also be used.

Examples of other suitable absorbent materials include comminuted wood pulp, which is generally referred to as airfelt; cotton fibers or cotton lintels; creped cellulose wadding; meltblown polymers including coform; chemically stiffened, modified, or cross-linked cellulosic fibers; synthetic fibers such as crimped polyester fibers or rayon fibers; peat moss; tissue including tissue wraps and tissue laminates; absorbent foams; absorbent sponges; superabsorbent polymers (in granular or fibrous forms); absorbent gelling materials; or any equivalent material or combination of materials, or mixtures of these. Preferred absorbent materials include cotton batts, folded tissues, woven materials, nonwoven webs, needle punched rayon, and thin layers of foam. The central absorbent portion 28 may comprise a single material or a combination of materials.

Figure 3:
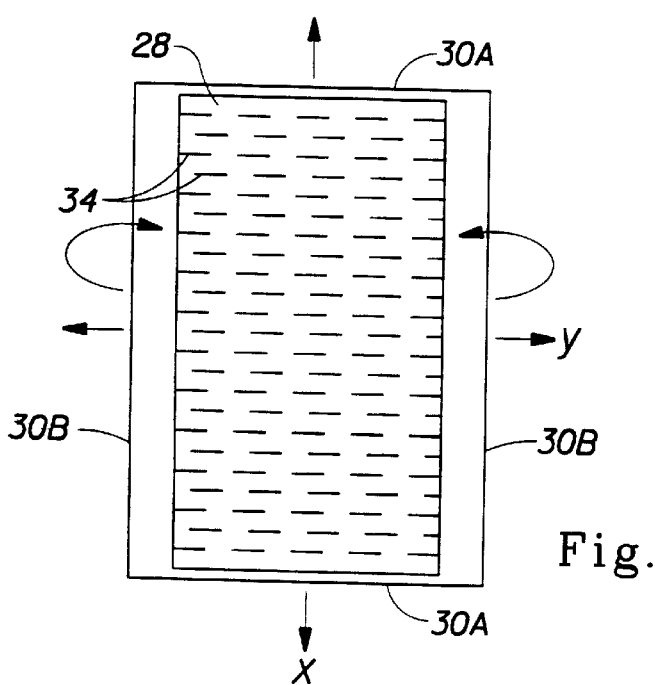
FIG. 3 is a plan view of the materials comprising the absorbent interlabial device of the present invention prior to folding to form the device.

In the preferred embodiment shown in FIGS. 1 and 2, the central absorbent portion 28 is formed of a soft, flexible absorbent material. The flexibility of the central absorbent portion 28 is preferably increased by providing the central absorbent portion with a series of slits 34 as shown in FIG. 3. FIG. 3 shows a slitted central absorbent portion 28. FIG. 3 also shows the central absorbent portion 28 overlaying the topsheet 30 prior to the topsheet 30 and central absorbent portion 28 being folded so as to define the central groove 32. A more complete description of a slitted absorbent material which is suitable for use in the present invention is found in U.S. Pat. No. 5,611,790 issued to Osborn, III et al. on Mar. 18, 1997.

The central absorbent portion 28 preferably at least partially comprises biodegradable materials. As used herein, the term "biodegradable materials" refers to a material having greater than or equal to about 70% biodegradation (percentage of theoretical carbon dioxide evolution) after 28 days when measured according to the Sturm Test which has been designated Method 301B by the Organization for Economic Cooperation and Development. Preferably, the materials comprising the present invention have a biodegradation of greater than about 80% and, more preferably, biodegradation is greater than or equal to about 90%.

Preferably, the overall interlabial device 20 is toilet disposable. The term "toilet-disposable" as used herein includes the following characteristics of an absorbent interlabial device 20: flushability, dispersibility, and biodegradability. As used herein, the terms "flushable" and "flushability" refer to a product's ability to pass through typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product such as an absorbent interlabial device 20, is set out in the TEST METHODS section of this specification.

The term "dispersible" as applied herein to an absorbent interlabial device 20 refers to an article which will disperse into at least two fragments in mildly agitated water. Such a device will break into pieces in a conventional toilet and/or domestic plumbing system.

The term "biodegradable" as used herein refers to an absorbent device which is preferably at least partially constructed of biodegradable materials. While biodegradable materials are preferred for the interlabial device 20. It is not necessary that each and every material used be biodegradable. For example, the device 20 may comprise superabsorbent particles which do not biodegrade, and this will not affect the ability of the overall device 20 to preferably remain toilet-disposable and to be effectively processed in a sewage treatment system.

The main portion 26 of the interlabial device 20 of the present invention also comprises a liquid pervious topsheet such as topsheet 30. The topsheet 30 should be compliant, soft feeling, and non-irritating to the wearer's skin. The topsheet 30 should further exhibit good strikethrough and a reduced tendency to rewet permitting bodily discharges to rapidly penetrate it and flow toward the central absorbent portion 28, but not allowing such discharges to flow back through the topsheet 30.

A suitable topsheet 30 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers. When the topsheet 38 comprises a nonwoven web, the web may be spunbonded, carded, wet-laid, meltblown, hydrogentangled, combinations of the above, or the like.

A particularly suitable topsheet 30 for use in the present invention is formed of rayon with a basis weight of about 18 g/m$^2$ and is available from Veratec, Inc. of Toronto, Ontario, Canada. This material is particularly suitable for use as a topsheet 30 becuase it is biodegradable.

The topsheet 30 may also comprise an apertured formed film. Apertured formed films are pervious to body exudates and, if properly apertured, have a reduced tendency to allow liquids to pass back through them. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. A suitable topsheet 30 for the present invention is the formed film described in one or more of the above patents and marketed on sanitary napkins by The Procter & Gamble Company of Cincinnati, Ohio as the "DRI-WEAVE" topsheet.

Another suitable topsheet 30 for the present invention is made in accordance with U.S. Pat. Nos. 4,609,518 and 4,629,643 both issued to Curro et al. on Sep. 2, 1986 and Dec. 16, 1986, respectively. Such a formed film is manufactured by Tredegar Corporation of Terre Haute, Ind.

In a preferred embodiments of the present invention, the outwardly facing (i.e. body facing) surface of the formed film topsheet 30 is hydrophilic so as to help liquid to transfer through the topsheet faster than if the outwardly facing surface was not hydrophilic. This hydrophilicity diminishes the likelihood that menstrual fluid will flow off the topsheet 30 rather than flowing into and being absorbed by the central absorbent portion 28. In preferred embodiments, surfactant is incorporated into the polymeric materials of the formed film topsheet 30. Additionally, the outwardly facing surface of the topsheet 30 can be made hydrophilic by treating it with a surfactant such as is described in U.S. Pat. No. 4,950,254 issued to Osborn, III.

The topsheet 30 is wrapped around the central absorbent portion 28 and is optionally also joined to the same. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The topsheet 30 may be joined to the central absorbent portion 28 by any variety of means. For example, as shown in FIGS. 1–2 the topsheet 30 may be joined to the central absorbent portion 28 thorough the use of stitching 36 (such as with cotton or rayon thread). Alternatively, the topsheet 30 may be joined to the central absorbent portion 28 using any suitable adhesive, thermal bonding, fusion bonding, or any other suitable means known in the art for joining such materials. Regardless of whether or not the topsheet is 30 joined to the central absorbent portion 28, the topsheet 30 will be wrapped around the central absorbent portion 28 as described above. The topsheet 30 should also be secured in a manner which acts to contain the central absorbent portion 28 in a wrapped relationship with respect to the topsheet 30 and maintains the structure of the central groove 32, previously described.

Figure 5:
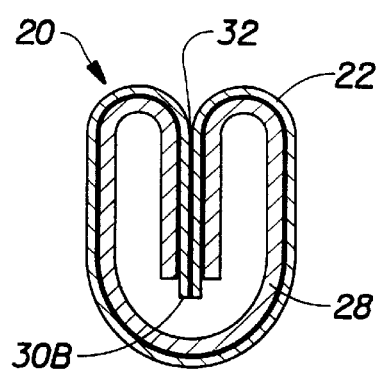
FIG. 5 is a cross-sectional end view of the device shown in FIG. 4

FIG. 2 and FIG. 5 both show longitudinal cross-sectional views of embodiments of the absorbent interlabial device 20 of the present invention. FIG. 5 shows the central absorbent portion 28 and the topsheet 30 wrapped around the central absorbent portion and folded in accordance with the present invention as previously described. FIG. 2 also shows the central absorbent portion 28 and the topsheet 30 folded and wrapped as in FIG. 5, but also shows additional optional components of the absorbent interlabial device 20 not shown in FIG. 5. These optional components will be more fully described below. As seen in FIGS. 2 and 5, the longitudinal cross section of the absorbent interlabial device 20 is substantially cardiod or heart-shaped. Other longitudinal cross-sectional shapes which provide the central groove 32 feature, described above, may also be used.

In addition to the topsheet 30 and the central absorbent portion 28, the main portion 26 of the absorbent interlabial device 20 may also contain several optional components. For example, as shown in FIG. 2, the absorbent interlabial device 20 may be provided with a secondary topsheet 38 disposed between the topsheet 30 and the central absorbent portion 28. The secondary topsheet 38 acts to pull fluid quickly from the topsheet 30 and to direct it to the central absorbent portion 28 for storage. Preferably, the secondary topsheet 38 has some initial absorbent capacity, but quickly releases absorbed fluids to the central absorbent portion 28. Suitable materials for the secondary topsheet 38 include rayon, polyester, rayon blended with polypropylene, blends of polyester, or some combination of these. A rayon and polypropylene blend having a basis weight of about 68 grams per square meter is in preferred embodiments as a material for the secondary topsheet 38.

The secondary topsheet 38, if used, may be attached to one or both of the central absorbent portion 28 or the topsheet 30. Any of the methods of attachment described above for the topsheet 30 are applicable to the secondary topsheet 38. In the preferred embodiment shown in FIGS. 1 and 2, the secondary topsheet 38 is joined to the topsheet 20 and the central absorbent portion 28 by stitches 36. These stitches 36 also serve to maintain the shape of the main portion 26 of the interlabial device 20 thereby maintaining the structure of the central groove 32 when the device 20 is worn.

The absorbent interlabial device 20 may also comprise a liquid impervious backsheet 40 which is joined to at least a portion of the topsheet 30. In the preferred embodiment shown in FIGS. 1 and 2, the backsheet 40 is joined to the topsheet 30 at the bottom surface 24 of the absorbent interlabial device 20. If the interlabial device 20 does not comprise flexible extensions 42 (more fully described below), the backsheet 40 may be directly attached to the topsheet 30 at the bottom surface 24 of the device 20. If flexible extensions 42 are used, these may comprise a single web of material, a portion of which is disposed between the topsheet 30 and the backsheet 40. Such an arrangement is shown in FIGS. 1 and 2 and is described more fully below. The backsheet 40 may be joined to the absorbent interlabial device by any suitable conventional means known in the art.

If a backsheet is used, the backsheet 40 could be impervious or semi-pervious to liquids (e.g., menses and/or urine) and is preferably flexible. As used herein, the term "flexible" refers to materials which are compliant and will readily conform to the general shape and contours of the human body. The backsheet 40 prevents the exudates absorbed and contained in the main portion 26 from wetting articles which contact the absorbent interlabial device 20 such as the wearer's undergarments. The backsheet 40 also assists the main portion 26 in preventing the wearer's body from being soiled by exudates. Additionally, use of the backsheet 40 may provide an improved surface for the wearer to grasp between the fingers as the absorbent interlabial device 20 is inserted, or as the device is optionally removed with the fingers.

The backsheet 40 may comprise a woven or nonwoven material, polymeric films such as thermoplastic films of polyethylene or polypropylene, or composite materials such as a film-coated nonwoven material. Preferably, the backsheet 40 is a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-1401. The backsheet 40 may permit vapors to escape from the main portion 26 (i.e. it may be breathable) while still preventing exudates from passing through the backsheet 40.

As shown in FIGS. 1 and 2, the absorbent interlabial device 20 may also comprise a pair of flexible extensions 42. The flexible extensions 42 are joined to the main portion 26 and extend downwardly and outwardly therefrom beginning at a point near the top surface 22 of the main portion 26 of the interlabial device 20. In the preferred embodiment shown in FIGS. 1 and 2, the flexible extensions 42 are generally rectangular in shape. Other shapes are also possible for the flexible extensions 42 such as semi-circular, trapezoidal, or triangular. The flexible extensions 42 preferably range from about 30 mm to about 70 mm in length, more preferably about 50 mm in length.

While the flexible extensions 42 can have a length (measured in the x-direction) which is the same as or longer than the main portion 26, preferably they have a length which is shorter than the main portion 26 of the absorbent interlabial device 20. The width of each flexible extensions refers to the distance from the uppermost point attachment of flexible extension 42 to the main portion 26 (or the proximal end 42A of the flexible extension 42) to the distal end (or free end) 42B of the flexible extension 42. The width of the flexible extensions 42 is preferably about equal to or slightly less than the height of the main portion 26 as described above. In the preferred embodiment shown in FIGS. 1 and 2, the width of the flexible extensions 42 is about 13 mm to 20 mm, more preferably about 17 mm.

The caliper of the flexible extensions is preferably less than or equal to about 3 mm, more preferably less than or equal to about 2 mm, and most preferably less than or equal to about 1 mm.

The flexible extensions 24 may be constructed of a tissue layer. A suitable tissue is an airlaid tissue available from Fort Howard Tissue Company of Green Bay, Wis., and having a basis weight of 35 lbs./3000 sq. ft. Another suitable airlaid tissue is available from Merfin Hygienic Products, Ltd., of Delta, British Columbia, Canada, having a basis weight of 61 g/m$^2$ and having the designation grade number 176. These tissues may be coated with a layer of nonwoven material which is heat sealed to the body-contacting side of the tissue to help prevent the tissue layer from fragmenting in the labia. A suitable nonwoven material is known as COROLIND and is available from Corovin, GmbH, Peine, Germany. The flexible extensions 42 may optionally be backed with a layer of material which is impervious or semi-pervious to body exudates such as, wax, polyethylene, polypropylene, or a polyvinylalchohol. Additionally, the flexible extensions 42 may be coated with an emollient to improve the ease of insertion of the interlabial device 20 and to improve the comfort of wearing the device 20.

In the preferred embodiment shown in FIGS. 1 and 2, the pair of flexible extensions 42 may comprise a single sheet of material extending to either side of the longitudinal centerline L of the absorbent interlabial device 20. Alternatively, the pair of flexible extensions 42 may comprise separate sheets of material independently joined to the main portion 26 of the interlabial device 20. Preferably, the flexible extensions 42 are arranged symmetrically about the longitudinal centerline L of the interlabial device 20.

The flexible extensions 42 may be joined to the main portion 26 of the interlabial device 20 by any variety of means. For example, in the preferred embodiment shown in FIGS. 1 and 2, the flexible extensions 42 may be joined to the main portion 26 of the interlabial device 20 near the top surface 22 with stitching 36. Alternatively, the flexible extensions 42 may be attached to the main portion 26 of the device 20 using any suitable adhesive. Such an adhesive may extend continuously along the length of the main portion 26 or it may be applied in a "dotted" fashion at discrete intervals. Other suitable means of attachment include thermal bonding, fusion bonding, or any other suitable means known in the art for joining such materials.

As shown in FIGS. 1 and 2, the flexible extensions 42 are attached to the main portion 26 near the top surface 22 of the interlabial device 20. The flexible extensions 42 extend downwardly and outwardly from the main portion 26 to a free end 42B which is unattached to the main portion 26. The flexible extensions 42 may be biased slightly outward from the main portion 26 so as to tend to keep the extensions 42 in contact with the inner surfaces of the labia when the absorbent interlabial device 20 is in place. Additionally, the naturally moist surfaces of the labia will have a tendency to adhere to the material comprising the flexible extensions 42 further tending to keep them in contact with the inner surfaces of the labia. Preferably, the flexible extensions 42 should be capable of motion from a position where the free ends of the flexible extensions 42 lie adjacent to the main portion 26 to a position where the flexible extensions 42 extend directly out from the main portion 26 in the transverse direction.

The flexible extensions 42 should be of sufficient width and flexibility to allow the flexible extensions 42 to cover the wearer's fingertips as the absorbent interlabial device 20 is inserted into the wearer's interlabial space. Additionally, the flexible extensions 42 should be capable of moving with the inner surfaces of the wearer's labia to maintain contact with the same. The flexible extensions 42 help keep the main portion 26 in place throughout a range of wearer motions such as squatting.

The flexible extensions 42 may be hydrophillic or hydrophobic. The flexible extensions 42 may be treated to make them less hydrophillic than the main portion 26. The hydrophillicity of a material is generally expressed in terms of its contact angle. Thus, the flexible extensions 42 may have an advancing contact angle greater than the advancing contact angle of main portion 26, such that fluid is preferentially directed toward and absorbed by the main portion 26. The flexible extensions 42 may be either absorbent or nonabsorbent. Preferably, the flexible extensions 42 have at least some absorbency. The majority of the fluid absorbed and retained by the absorbent interlabial device 20, howver, will preferably ultimately be retained in the main portion 26, particularly in the central absorbent poriton 28. For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/ Princeton Publications, Publication Number 459, entitled "A Microtechnique for Determining Surface Tension," published in April 1992, and Publication Number 468 entitled, "Determining Contact Angles Within Porous Networks," published in January, 1993, both edited by Dr. H. G. Heilweil.

The flexibility of both the main portion 26 and the flexible extensions 42 is important for product comfort. The interlabial device 20 should be provided with both compressibility and bendability. Bendability refers to the ability of the device 20 to bend about the longitudinal axis L and/or the transverse axis (i.e. the "y-direction"), of the interlabial device 20 when subject to a bending force. Compressibilty refers to the ability of the interlabial device 20 to deform locally in response to a compressive force, tending to give the device 20 a soft, compliant feel. Providing the central absorbent portion 28 with slits 34 as described above improves both the bendability and compressibility of the interlabial device 20. Materials chosen for the components of the interlabial device 20 should be selected to provide an overall device 20 which is highly flexible so as to improve wearer comfort, yet sufficiently rigid so as to be easily placed between the folds of the labia and maintain its shape in use. If the absorbent interlabial device 20 is too flexible, the device is not conveniently or easily placed between the folds of the labia, if it is too stiff, the device is uncomfortable and when the user is in a sitting position, the device 20 can be forced forward against the clitoris causing discomfort.

Preferably, the interlabial device 20 is comprised of more lofty material near the top surface 22 and more dense material near the bottom surface 24. Such an arrangement provides a large to small capillary structure as fluid travels downward into the central groove 32 and into the central absorbent portion 28 of the interlabial device 20. Additionally, this arrangement of lofty material on top and more dense material on the bottom of the interlabial device 20, results in a product which is more conformable at the body contacting areas, thus improving wearer comfort.

The absorbent interlabial device 20 is preferably also provided with sealed ends 44 as shown in FIG. 1. Any suitable means of sealing the ends of the interlabial device 20 such as heat sealing may be used. In the preferred embodiment shown in FIG. 1, the sealed ends 44 of the interlabial device 20 are oriented in both the "x" and the "z" directions. That is, the distance between the sealed ends 44 is shorter at the top surface 22 of the interlabial device 20 than the distance between the sealed ends 44 at the bottom surface 24 of the interlabial device 20. This arrangement results in an interlabial device which has a trapezoidal-shaped transverse cross section, as shown in FIG. 1. Alternatively, the sealed ends 44 may be rounded as seen from a transverse cross-sectional view of the interlabial device 20. Preferably, the ends 44 are split apart (i.e. not sealed) in the vicinity of the top surface 22 of the interlabial device 20. In the preferred embodiment shown in FIG. 1, the sealed ends 44 are sealed up to a point about 4 mm from the top surface 22 of the interlabial device 20.

The end sealing feature of the absorbent interlabial device 20 shown in FIG. 1 improves the comfort associated with the wearing of the device 20. When the ends are sealed and shaped, they are more easily compressible or collapsible when pressed. This allows the device 20 to be less bulky at the sealed ends 44 and provides improved comfort during wear.

The strength and stiffness of the flexible extensions 42 are important characteristics of their design. If the flexible extensions 42 have a wet burst strength of less than or equal to about 15 grams, they will tend to shred and may leave pieces remaining in the wearer's interlabial space. Similarly, if the flexible extensions 42 are as stiff as a manila file folder, they do not provide sufficient flexibility to dynamically adjust to the motion of the labia. The stiffness of the flexible extensions 42 is measured as a bending resistance. Preferably, the flexible extensions 42 have a bending resistance of less than about 25 gm measured using the Three Point Bend Test. More preferably, the flexible extensions 42 have a bending resistance of less than or equal to about 5 gm. A description of the Three Point Bend Test is contained in the Test Methods section, below. The flexible extensions 42 also have an inherent strength, so that during application and wear they do not tear. The wet strength for the flexible extensions 42 should exceed 15 grams, and preferably exceeds 150 grams, and most preferably exceeds 300 grams. The wet strengths given above are measured using the Wet Burst Test which is described in greater detail in the Test Methods section, below.

The structure of the absorbent interlabial device 20 of the present invention allows for an easier manufacture using current web handling technology than that associated with the manufacture of a cylindrical-shaped shaped device (i.e. a product without the central groove 32 of the present invention). The interlabial device 20 of the present invention may be manufactured by first assembling the materials which make up the components of the device 20 in a layered configuration as shown in FIG. 7.

The following describes one non-limiting example of assembly of an absorbent interlabial device 20 of the present invention. If a backsheet 40 is to be used it may be provided in strips of about 120 mm×16 mm. The strip of backsheet 40 material is provided such that the garment facing side of the material is facing downward. If the device 20 is to have flexible extensions 42 these may be provided next in the form of a rectangular segment of material about 120 mm×51 mm in size. The flexible extension 42 material is placed on top of the backsheet 40 material such that its longer dimension is perpendicular to the longer dimension of the backsheet material 40.

The topsheet 30 material may be cut into rectangular segments of about 127 mm×86 mm. The webs of topsheet 30 material are placed with the body facing side down, on top of the flexible extension 42 material and the backsheet material 40, if provided. If the device 20 is to have a secondary topsheet 38, the material for the secondary topsheet 38 may be cut into rectangular segments of about 95 mm×79 mm. The secondary topsheet 38 layer is placed on top of the topsheet 30 layer. The central absorbent portion 28 may be provided with slits 34 and cut into rectangular segments of about 92 mm×64 mm. The central absorbent portion 28 layer is placed on top of the secondary topsheet 38 layer, if provided. Otherwise, the central absorbent portion 28 layer will rest directly on the topsheet 30 material.

Figure 4:
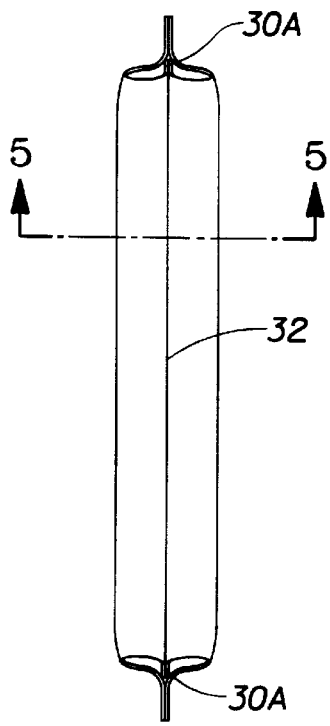
FIG. 4 is a top plan view of the materials shown in FIG. 3 after having been folded and secured to form an interlabial absorbent device in accordance with the present invention.
Figure 7:
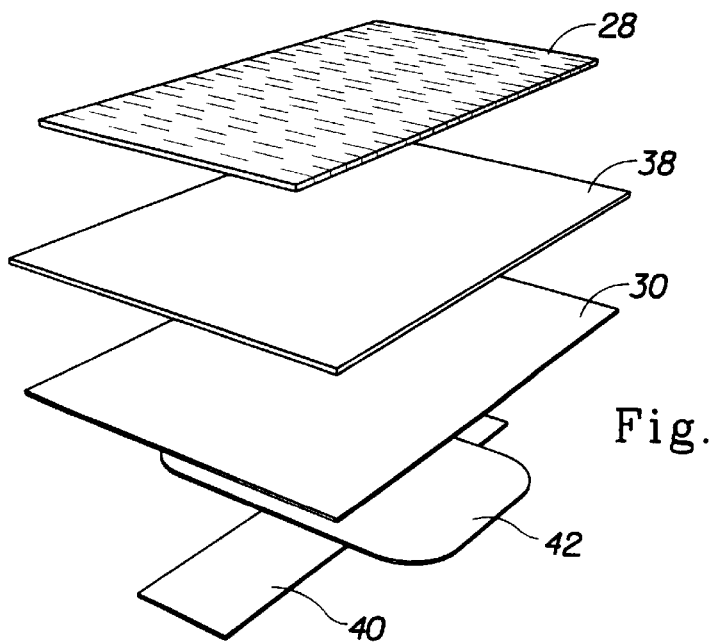
FIG. 7 is an exploded plan view showing the assembly of the materials comprising a preferred embodiment of the absorbent interlabial device of the present invention in a layered configuration prior to the folding and securing of the layers to form the completed device.

Once the materials are layered in the configuration shown in FIG. 7, the layers are folded and secured to form the absorbent interlabial device 20. FIGS. 3–5 show how the layers are folded to form the completed device 20. For simplicity, FIGS. 3–5 show a device 20 comprising only a topsheet 30 layer and central absorbent portion 28. FIG. 3 shows the composite layers prior to any folding. As shown in FIG. 3, the central absorbent portion 28 is overlaying the topsheet 30 layer. Both layers are rectangular segments. The longitudinal edges 30A of the topsheet 30 will become the ends of the device 20 after folding and securing of the layers as shown in FIG. 4. Similarly, the transverse edges 30B of the topsheet 30 will be folded together and secured to form the central groove 32 of the present invention as shown in FIG. 5.

Figure 3A:
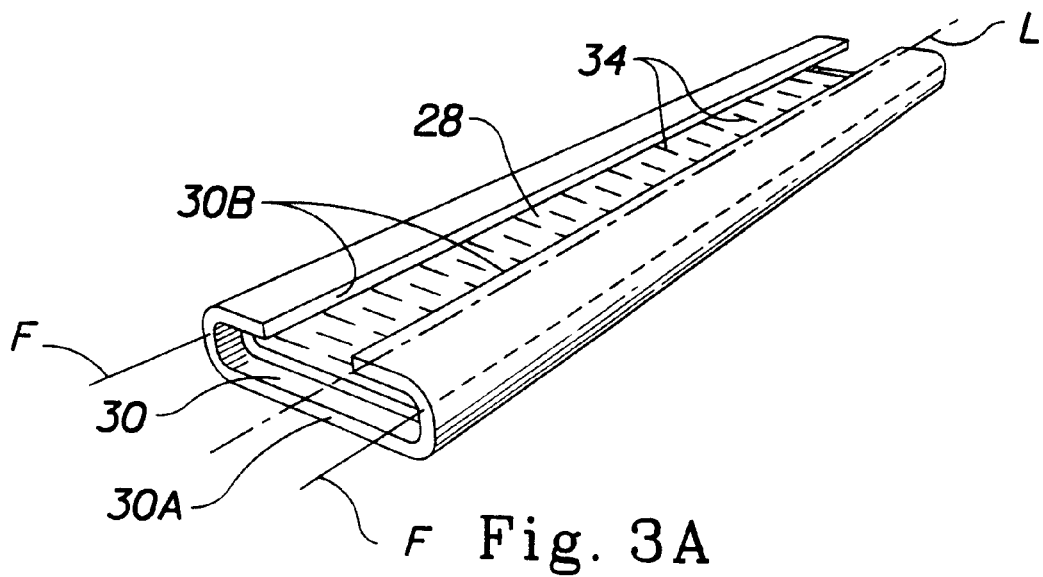
FIG. 3A is is a perspective view of the composite materials shown in FIG. 3 after the side margins have been folded in a first folding operation.
Figure 3B:
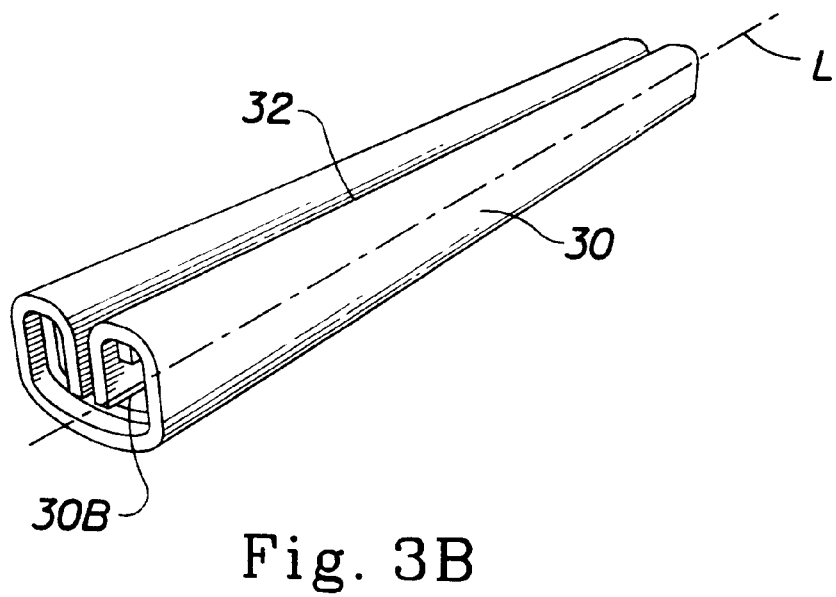
FIG. 3B is a perspecive view of the composite materials shown in FIG. 3 after it has been folded in a second folding operation.

The transverse edges 30B of the layered materials are folded as a unit as shown in FIG. 3A along folding axes F in a first folding operation to form a "C"-folded strucuture. The device 20 then undergoes a second folding operation shown in FIG. 3B wherein the two transverse edges of the device 20 after the first folding operation are folded upwards toward each other. This second folding operation takes place along second fold line F shown in FIG. 3B. After this second folding operation, the topsheet 30 layer is in a wrapped configuration around the central absorbent portion 28 as shown in FIG. 4. This two step folding, the end result of which is shown in FIG. 4 defines the central groove 32 which is more clearly shown in FIG. 5. The transverse edges 30B of the topsheet may be secured using any suitable means known in the art (such as stitches or adhesive, not shown) to retain the device 20 in such folded configuration. The longitudinal edges 30A of the topsheet may be trimmed and heat sealed to form the shaped end seals 44 previously described and shown in FIG. 1.

Figure 6:
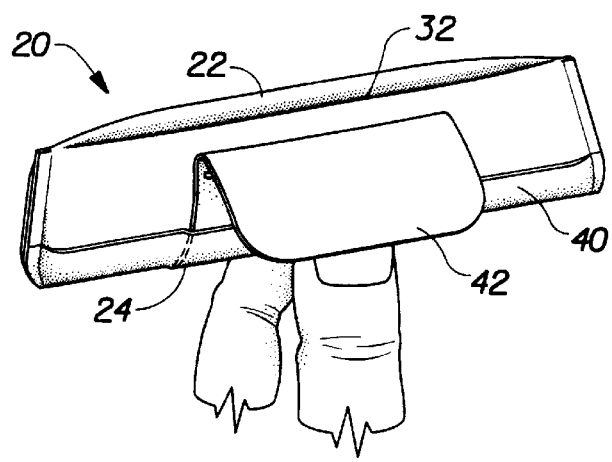
FIG. 6 is an end view of one embodiment of the absorbent interlabial device of the present invention showing flexible extensions covering the wearer's fingertips.
Figure 8:
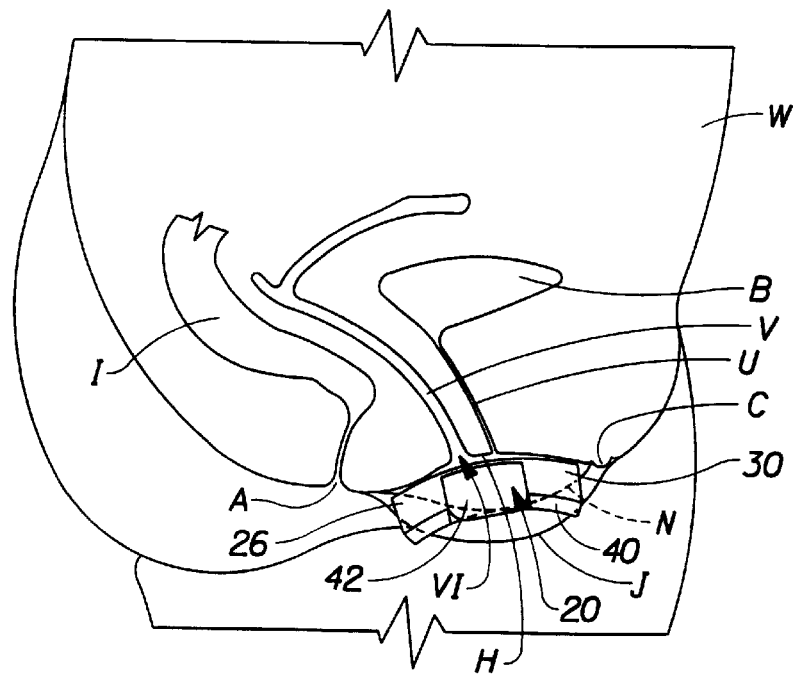
FIG. 8 is a cross-sectional saggital view of a human female wearer showing the placement of the absorbent interlabial device in the wearer's interlabial space.

As previously discussed, the absorbent interlabial device 20 of the present invention is designed to be placed within the interlabial space of a wearer. To use the absorbent interlabial device 20 of the present invention, the wearer holds the main portion 26 between her fingers. As shown in FIG. 6, the flexible extensions 42 are spread apart so as to cover the tips of the wearer's fingers during insertion. This feature provides for a hygienic insertion of the absorbent interlabial device 20 of the present invention. The interlabial device 20 is inserted with the top surface 22 inserted first and farthest into the interlabial space. The wearer may assume a squatting position during insertion to assist in spreading the labial surfaces. FIG. 8 shows a preferred embodiment of the absorbent interlabial device 20 of the present invention inserted into the interlabial space of a wearer W. The urogenital members shown in FIG. 8 include the bladder B, the vagina V, the urethra U, the clitoris C, the large intestine I, the anus A, the vaginal introisus VI, the hymenal ring H, the labia minora N, and the labia majora J. FIG. 8 shows the relationship of these anatomical features of the wearer W to the absorbent interlabial device 20 when the device is properly inserted for use. Once the absorbent interlabial device 20 is inserted, the flexible extensions 42 tend to adhere to the inside surfaces of the labia.

The interlabial device 20 is preferably at least partially retained in place by exerting a slight laterally outwardly-oriented pressure on the inner surfaces of the wearer's labia minora, labia majora, or both. Additionally, the product may also held by attraction of naturally moist labial surfaces to the material comprising the flexible extensions 42 or the topsheet 30, or both. Optionally, the flexible extensions 42, the topsheet 30, or both, may be provided with a bio-compatible adhesive to assist the adhesion of the device 20 to the inside surfaces of the wearer's labia. The strength of such an adhesive should be selected to assist the absorbent interlabial device 20 in staying in place, while still allowing for reliable, and comfortable removal of the device from the wearer's interlabial space. A suitable adhesive strength would allow the interlabial device 20 to remain in place against a pressure tending to remove it where the pressure was in the range of about 10 cm to 150 cm of water.

The absorbent interlabial device 20 is believed to differ from the prior art in a number of respects. The absorbent interlabial device 20 of the present invention is provided with a central groove 32. This groove serves to assist the device 20 in more rapidly acquiring fluid, particularly more viscous fluids, than prior art devices. Additionally, the size and shape of the device combined with the size and shape of the central groove 32 contributes to product comfort by allowing the device 20 to more easily fit around the clitoris. The design of the interlabial device 20 of the present invention provides an interlabial product which is conformable and compressible, and therefore comfortable to wear, yet large enough to achieve higher absorption capacities than many prior art products.

The absorbent interlabial device 20 of the present invention is preferably adapted to consistently block the wearer's urethra and orifice of the vagina upon insertion. As a result, the absorbent interlabial device 20 of the present invention is believed to be expelled by urination more reliably than the prior art devices. As noted previously, when flexible extensions 42 are provided, these cover the wearer's fingertips during insertion (as shown in FIG. 6) thereby providing for a more hygienic insertion than is achieved with prior art devices. Optionally, the absorbent interlabial device 20 may be removed by grasping the bottom surface 24 of the main portion 26 with the fingers. Again, if provided, the flexible extensions 42 continue to cover the fingertips thereby allowing for a more hygienic removal of the absorbent interlabial device 20 than is achieved with prior art devices.

The absorbent interlabial device 20 can be worn as a "stand alone" product. Alternatively, it can be worn as a back up to a tampon, or in combination with a sanitary napkin, pantiliner, or incontinence pad for menstrual or incontinence use. If the absorbent interlabial device 20 is used with a sanitary napkin, the sanitary napkin can be of any thickness. Use with a sanitary napkin may be preferred at night to reduce rear soiling. The interlabial device 20 can be worn in conventional panties, or it can be used with menstrual shorts.

Numerous alternative embodiments of the absorbent interlabial device of the present invention are possible. For example, the absorbent device designed to be removed by urination, although an alternative extraction string or loop may be used. The interlabial device may also be used with medicinal treatments. The device may be constructed of materials which are biodegradable and/or which will fragment in water with agitation (as in a toilet). The absorbent interlabial device 20 may also be constructed with a plurality of slits in the main portion 26 so as to permit bending of the product in multiple independent directions. Such a structure allows the product to more easily respond to the stresses associated with body movements. The top surface 22 of the structure may have one or more slits or have other regions of preferred bending so that product may easily adjust to the vertical pressure against the pelvic floor, to help accommodate the non-linear surface of the pelvic floor between the clitoris and the perineum. The flexible extensions 42 of the interlabial devive 20 may also act as a spring in both wet and dry conditions such that the sides of the product tend to expand outward pressing against the lateral walls of the labial vestibule, thereby, holding the product in place. In addition, the flexible extensions 24 may have the ability to act as a "spring" when wet, such as when the product is saturated with liquid. Structures, such as polyurethane foams can provide these properties.

Test Methods

Absorbent Capacity

Absorbent capacity may be determined as follows. The test is performed on samples that have been conditioned by leaving them in a room at 50% relative humidity and at 73° F. for a period of two hours prior to the test. The test should be performed under similar conditions.

The article is weighed to the nearest 0.1 gram. The article is then submerged in a beaker of sterile 0.9% saline solution (obtainable from the Baxter Travenol Company of Deerfield, Ill.), such that the article is totally submerged and is not bent or otherwise twisted or folded. The article is submerged for 10 minutes. The article is removed from the saline and suspended for two minutes in a vertical position to allow the saline to drain out to the article. The article is then placed body facing surface down onto an absorbent blotter, such as the filter paper #631 available from the Filtration Science Corp., Eaton-Dikeman Division of Mount Holly Springs, Pa. A uniform 17.6 grams per square centimeter load is placed over the article to squeeze excess fluid out. The absorbent blotter is replaced every 30 seconds until the amount of fluid transferred to the absorbent blotter is less than 0.5 grams in a 30 second period. Next, the article is weighed to the nearest 0.1 gram and the dry weight of the article is subtracted. The difference in grams is the absorbent capacity of the article.

Three Point Bend Test

The Three Point Bend Test is performed on samples that have been conditioned by leaving them in a room at 50% relative humidity and at 73° F. for a period of two hours prior to the test. The test should be performed under similar conditions.

Figure 9:
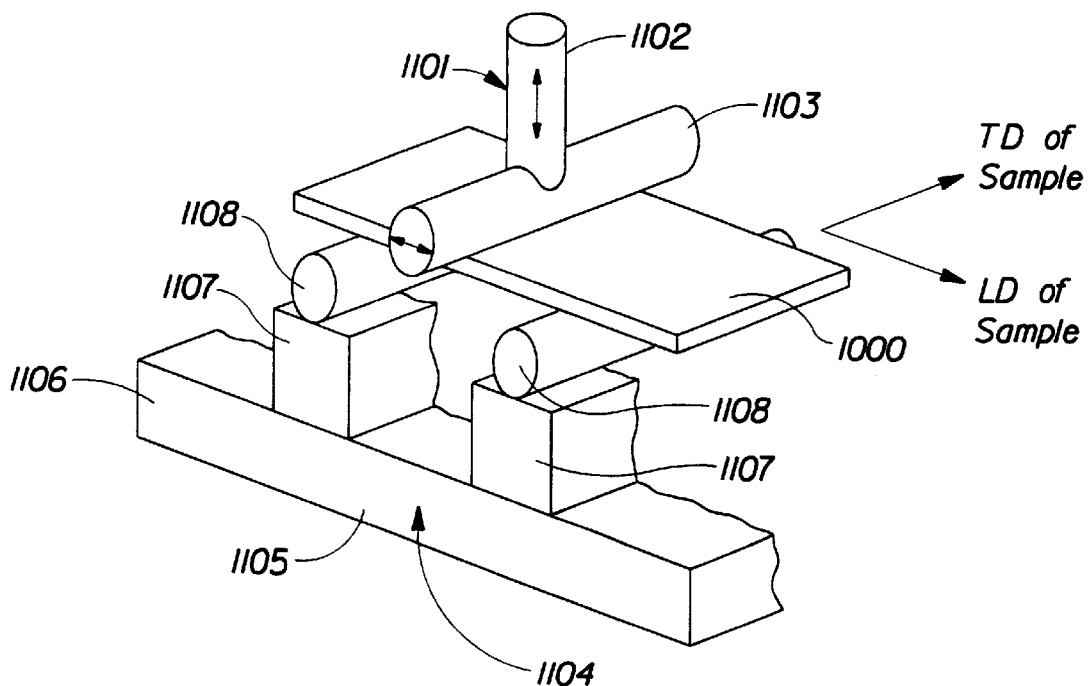
FIG. 9 is a schematic perspective view of the Three Point Bend Test apparatus.

The three point bend test uses an INSTRON Model 4502 tensile and compression testing machine, with a 10 N load cell, which is available from Instron Corporation of Canton, Mass. The test also uses a special displacement "T-rod" and a special test sample holder. As shown in FIG. 9, the "T-rod" 1101 comprises a pair of 6.40 mm diameter metal rods perpendicularly mounted together. The drive rod 1102 is about 125 mm long and the push rod 1103 is about 75 mm long. Preferably, the end of the drive rod 1102 is tapered to fit the circumference of the push rod 1103 and the two are glued, welded and/or screwed to each other. The opposite end of the drive rod 1102 is mounted to the crosshead unit of the INSTRON machine. The test sample holder 1104 comprises a fixture base 1105 for positioning and supporting a pair of supporting rods 1108. The fixture base 1105 comprises a base 1106 and two rectangular supports 1107 mounted in parallel on the base 1106. The base 1106 and the supports 1107 are each preferably made of LEXAN (plexiglas) plate of about 10 mm to about 13 mm thickness. A supporting rod 1108 of the same materials as the "T-bar" and about 150 mm long is mounted on each support 1107 of the fixture base 1105. The supporting rods 1108 are mounted so as to leave 10 mm of open space between them (measured at the point on each rod which is closest to the other). As shown in FIG. 9, the "T-rod" 1101 is centered between the supporting rods 1108.

The INSTRON machine is set for a crosshead speed of 2.0 in/min (50.8 mm/min). The INSTRON machine is set up so that the crosshead unit will travel 10 mm down and back for each sample tested.

Prior to testing of a sample, the T-rod 1101 is lowered until it is resting directly on top on one of the supporting rods 1108. The vertical position of the T-rod 1101 is "zeroed" when the load as it rests on supporting rod 1108 is about 1 $gram_f$. The T-rod 1101 is then raised 5 mm from this zero position and centered between both supporting rods 1108.

The sample 1000 to be tested is a piece of material taken from one of the flexible extensions 42. The sample 1000 taken should have a dimension of about 25 mm in the longitudinal direction LD and a dimension in the transverse direction of about 10 mm. The sample is placed so that the push rod 1103 is running parallel to a side of the sample that was oriented in the transverse direction TD.

The T-rod 1101 is then allowed to travel through a complete 10 mm cycle (i.e., 10 mm down and 10 mm back up). Consequently, the T-rod 1101 will make contact with the sample 1000 after about 5 mm and bend the sample about an additional 5 mm. The bending resistance is the peak force required to bend the sample as the T-rod travels through a complete 10 mm cycle.

Burst Strength Test

Overview

A test specimen, held between annular clamps, is subjected to increasing force that is applied by a 0.625 inch (1.59 cm) diameter, polished stainless steel ball. The burst strength is that force that causes the sample to fail. Burst strength may be measured on wet or dry samples.

Apparatus

| Apparatus | |
|---|---|
| Burst Tester | Intelect-II-STD Tensile Test Instrument, Cat. No. 1451-24PGB or the Thwing-Albert Burst Tester are both suitable. Both instruments are available from Thwing-Albert Instrument Co., Philadelphia, PA. |

-continued

| Apparatus | |
|---|---|
| | The instruments must be equipped with a 2000 g load cell and, if wet burst measurements are to be made, the instruments must be equipped with a load cell shield and a front panel water shield. |
| Conditioned Room | Temperature and humidity should be controlled to remain within the following limits:<br>Temperature: 73 ± 3° F. (23° C. ± 2° C.)<br>Humidity: 50 ± 2% Relative Humidity |
| Paper Cutter | Scissors or other equivalent may be used |
| Pan | For soaking wet burst samples, suitable to sample size |
| Solution | Water for soaking wet burst samples should be equilibrated to the temperature of the conditioned room. |
| Timer | Appropriate for measuring soak time |

Sample Preparation

1) Cut the sample to a size appropriate for testing (minimum sample size 4.5 in (11.4 cm)×4.5 in (11.4 cm)). If the sample to be tested is too small (e.g., a flexible extension with overall dimensions less than 4.5 in (11.4 cm)×4.5 in (11.4 cm)) a larger sample of the same material should be used to determine wet burst strength. Prepare a minimum of five samples for each condition to be tested.

2) If wet burst measurements are to be made, place an appropriate number of cut samples into a pan filled with temperature-equilibrated water.

Equipment Setup

1) Set the burst tester up according to the manufacturer's instructions. If an Intelect-II-STD Tensile Test Instrument is to be used the following are appropriate:

Speed: 12.7 centimeters per minute

Break Sensitivity: 20 grams

Peak Load: 2000 grams

2) Calibrate the load cell according to the expected burst strength.

Measurement and Reporting

1) Operate the burst tester according to the manufacturer's instructions to obtain a burst strength measurement for each sample.

2) Record the burst strength for each sample and calculate an average and a standard deviation for the burst strength for each condition.

3) Report the average and standard deviation for each condition to the nearest gram.

Report the average and the standard deviation for each group of four samples.

Water Dispersion Test

Apparatus

| Stirrer | Magnetic, Thermolyne type Model S7225 or 7200 (no substitutions). Permanently inscribe a circle 3.5 inches (8.9 centimeter) on the top surface of the stirrer. The center of the circle must be coincident with the geometric center of the stirrer. |
|---|---|
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL |

-continued

| | is suitable |
|---|---|
| Beaker | Kimax brand 2000 milliliter with spout (no substitution), Inscribe a fill mark at a height of 5.6 inches (14.3 centimeters) from the flat bottom of the beaker. Do not use any beaker not having a flat bottom. |
| Conditioned Room | Temperature and humidity should be controlled to remain within the following limits:<br>Temperature: 73 ± 3° F. (23° C. ± 2° C.)<br>Humidity: 50 ± 2% Relative Humidity |

Test Setup

1. Fill the beaker to the fill mark with 73±3° F. tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure

1. Hold a sample (e.g. an absorbent interlabial device 20) 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch. If the sample disrupts the rotation of the stirring bar, stop the stirrer, re-orient the bar, and immediately start the stirrer again.

Note: If the sample repeatedly becomes entangle with the stirring bar, the test may be performed by suspending the sample above the bottom of the beaker with a piece of cotton thread (for example, by tying the thread around the sample). Any suitable clamp and stand such as a ring clamp may be used for this purpose. The length of the thread and/or the height of the clamp should be adjusted such that when the thread is taught the sample is suspended in the water, but is not resting on the bottom of the beaker. The test procedure is otherwise unchanged.

4. Record the time required until the sample separates into at least two pieces. Separation does not include the disassociation of a few individual fibers from an otherwise intact sample. The time is the total time the sample is immersed in the water including the time the stirrer may have been stopped to re-orient the sample.
5. Repeat steps 1 through 4 with an additional 3 samples.

Calculation and Reporting

Calculate and report the mean and standard deviation of the water dispersibility time for the four samples tested.

Flushability Test

Overview

As noted above, the terms "flushable" or flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

Figure 10:
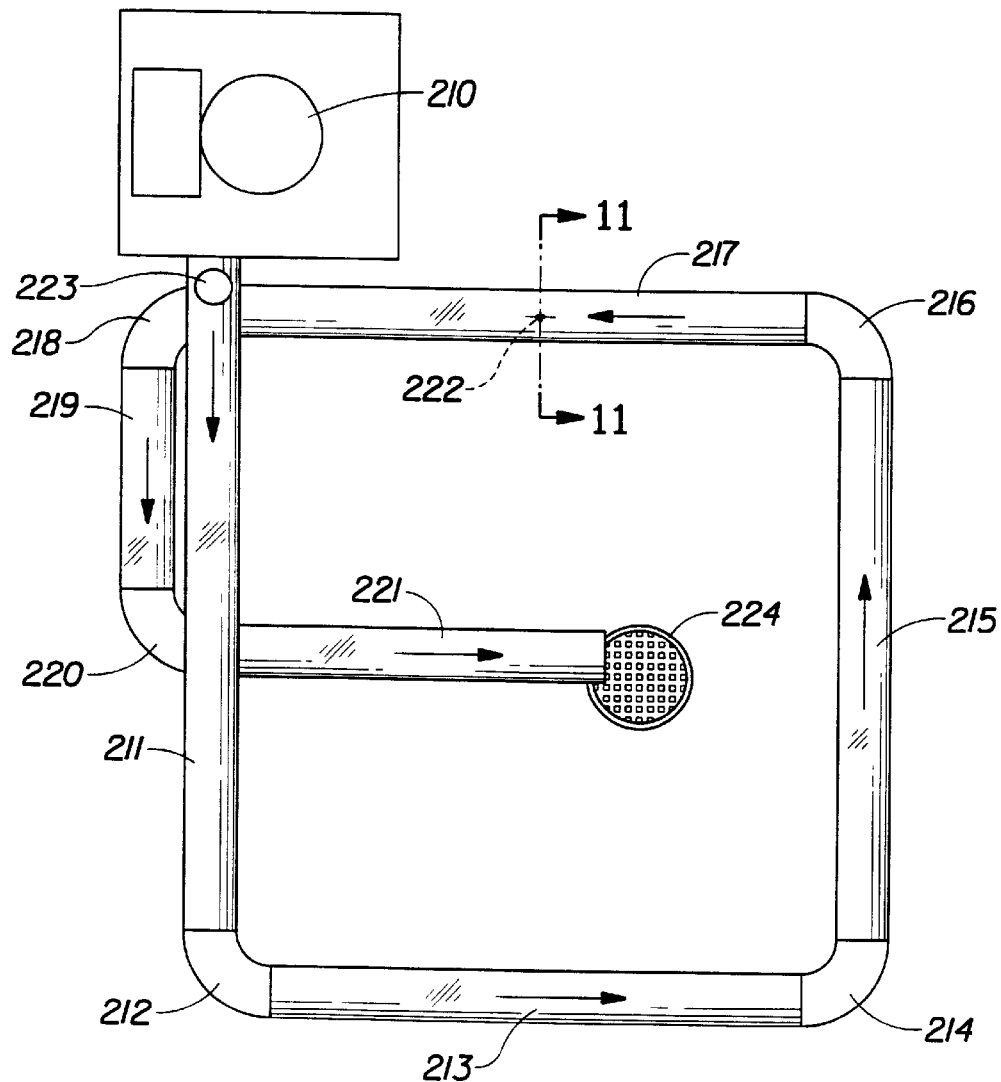
FIG. 10 is a plan view of an apparatus suitable for the flushability determination according to the method described in the TEST METHODS section, below.
Figure 11:
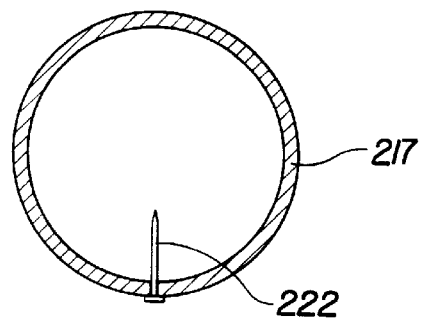
FIG. 11 is a cross-section of the flushability apparatus of FIG. 10 taken along line 11—11 thereof.

An apparatus suitable for the flushability test is shown in plan view in FIG. 10. The apparatus includes:
- a 3.5 gallon (13.2 liter) water saver siphon vortex toilet referred to as 210 (additional toilets can also be attached to the piping layout shown in FIG. 10 to evaluate the behavior of test samples using different flushing mechanisms such as commercial, pressure toilets);
- approximately 59 feet (18 meters) of 4 inch (10 cm) inside diameter acrylic pipe (As can be seen from FIG. 10, the piping is assembled in roughly a square configuration having linear runs 211, 213, 215, 217, 219, 221 approximately 10 feet (3 meters) long);
- a cast iron tee 223 slightly downstream of the toilet 210 that is open to the atmosphere for venting;
- five cast iron ninety degree elbows 212, 214, 216, 218, and 220;
- a snag 222 positioned vertically (FIG. 11) approximately 15 feet from the pipe's terminal end and approximately 1 inch (2.5 cm) long; and
- a screen 224 (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard CHARMIN® toilet tissue manufactured by The Procter & Gamble Company of Cincinnati, Ohio.

Synthetic Fecal Material: Prepared according to the method described below.

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1 (To be Performed First 6 Times for a Total of 30 Flushes)
1) Flush With Tissue Only—Take a drain line blockage reading 2 minutes after the water reaches the simulated obstruction, wait 1 additional minute, and move to step 2.
2) Flush With Empty Bowl. Take a drain line blockage reading 2 minutes after the water reaches the snag point and move to step 3.
3) Flush With Tissue and Catamenial Product—Take a drain line blockage reading 2 minutes after the water reaches the snag point, wait 1 additional minute, and move to step 4. If the catamenial product and/or tissue doesn't clear bowl after 1 flush, wait 2 minutes and flush again. If, after the second flush, the bowl and trap are not clear after flushing, the tissue and/or catamenial product is plunged into the drainage line manually and the flushing sequence will continue. After completion of each trial loading, the drainage pipe will be cleared prior to beginning subsequent testing.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be Performed 1 Time)
1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:
1) Incidence of failure (%) of catamenial product to clear bowl and trap in one flush
2) Incidence of failure (%) of catamenial product to clear bowl and trap in two flushes
3) Incidence of product on simulated snag
4) Maximum level (%) of drain line blockage
5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material

I. Materials Needed

Feclone synthetic fecal matter (900 grams); (Available from Siliclone Studio, Valley Forge, Pa. as product BFPS-7 dry concentrate)

Tap water at 100° C. (6066 grams)

II. Equipment Needed

Mixer (Available from Hobart Corp., Troy, Ohio as Model A200)

Extruder (Available from Hobart Corp., Troy, Ohio as Model 4812)

Disposable Centrifuge tubes with screw caps (50 ml) (Available from VWR Scientific, Chicago, Ill. as Catalog No. 21-008-176)

Water Bath to control temperature to 37° C.

III. Preparation

1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C. This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent device insertable into the interlabial space of a female wearer said absorbent device having a length, a width, and a height, said length, width, and height being oriented in an x-direction, a y-direction, and a z-direction, respectively, said absorbent device comprising:

a central absorbent portion; and a liquid pervious topsheet having two spaced apart transverse edges and two spaced apart longitudinal edges, said liquid pervious topsheet being wrapped around said central absorbent portion; wherein said length of said absorbent device is greater than said height of said absorbent device, said transverse edges of said liquid pervious topsheet are folded laterally inward over said central absorbent portion and downward substantially in said z-direction so as to define a central groove substantially oriented in said z-direction, said central groove extends in said x-direction along at least a portion of said length of said absorbent device, said central groove faces toward the vestibule floor of the wearer upon insertion of said absorbent device into the interlabial space of the wearer, and said central absorbent portion comprises a slitted core.

2. The absorbent device of claim 1 further comprising a liquid impervious backsheet joined to at least a portion of said liquid pervious topsheet.

3. The absorbent device of any of the preceding claims further comprising a secondary acquisition layer disposed between said central absorbent portion and said liquid pervious topsheet.

\* \* \* \* \*